United States Patent
Pianca et al.

(10) Patent No.: US 8,244,377 B1
(45) Date of Patent: Aug. 14, 2012

(54) FIXATION ARRANGEMENTS FOR IMPLANTABLE LEADS AND METHODS OF MAKING AND USING

(75) Inventors: Anne M. Pianca, Santa Monica, CA (US); Todd K. Whitehurst, Valencia, CA (US); Kristen N. Jaax, Santa Clarita, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 880 days.

(21) Appl. No.: 11/863,034

(22) Filed: Sep. 27, 2007

Related U.S. Application Data

(60) Provisional application No. 60/827,199, filed on Sep. 27, 2006.

(51) Int. Cl.
*A61N 1/05* (2006.01)
(52) U.S. Cl. ........................................ 607/126; 607/116
(58) Field of Classification Search .................. 607/126, 607/128, 130, 127, 129, 131
See application file for complete search history.

(56) References Cited

U.S. PATENT DOCUMENTS

| | | |
|---|---|---|
| 3,941,136 A | 3/1976 | Bucalo |
| 4,033,357 A | 7/1977 | Helland et al. |
| 4,135,518 A | 1/1979 | Dutcher |
| 4,257,428 A * | 3/1981 | Barton et al. ................. 607/128 |
| 4,301,815 A | 11/1981 | Doring |
| 4,475,560 A | 10/1984 | Tarjan et al. |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,722,353 A | 2/1988 | Sluetz |
| 4,796,643 A | 1/1989 | Nakazawa et al. |
| 4,867,164 A | 9/1989 | Zabara |
| 4,957,118 A | 9/1990 | Erlebacher |
| 5,025,807 A | 6/1991 | Zabara |
| 5,193,539 A | 3/1993 | Schulman et al. |
| 5,193,540 A | 3/1993 | Schulman et al. |
| 5,312,439 A | 5/1994 | Loeb |
| 5,314,457 A | 5/1994 | Jeutter et al. |
| 5,376,108 A | 12/1994 | Collins et al. |

(Continued)

FOREIGN PATENT DOCUMENTS

WO 98/37926 9/1998

(Continued)

OTHER PUBLICATIONS

He et al., "Implantable stimulator with Integrated Plastic Housing/Metal Contacts and Manufacture and Use," U.S. Appl. No. 11/238,240, filed Sep. 29, 2005. (Not Published).

(Continued)

*Primary Examiner* — Carl H Layno
*Assistant Examiner* — Allen Porter, Jr.
(74) *Attorney, Agent, or Firm* — Frommer Lawrence & Haug LLP; Bruce E. Black

(57) ABSTRACT

An implantable member has a body with a distal end portion and either a fixation portion of the body disposed near the distal end portion or a fixation device attached to a tip of the distal end portion of the body. The fixation portion can include at least one surface feature of the body that facilitates fixation of the implantable member within tissue when implanted.

13 Claims, 6 Drawing Sheets

U.S. PATENT DOCUMENTS

| | | | |
|---|---|---|---|
| 5,433,735 A | | 7/1995 | Zanakis et al. |
| 5,439,938 A | | 8/1995 | Snyder et al. |
| 5,454,840 A | | 10/1995 | Krakovsky et al. |
| 5,480,420 A | | 1/1996 | Hoegnelid et al. |
| 5,531,781 A | * | 7/1996 | Alferness et al. ............ 607/122 |
| 5,571,118 A | | 11/1996 | Boutos |
| 5,741,319 A | | 4/1998 | Woloszko et al. |
| 5,755,762 A | * | 5/1998 | Bush ............................ 607/122 |
| 5,775,331 A | | 7/1998 | Raymond et al. |
| 5,876,399 A | * | 3/1999 | Chia et al. ...................... 606/41 |
| 5,922,015 A | | 7/1999 | Schaldach et al. |
| 5,938,584 A | | 8/1999 | Ardito et al. |
| 6,051,017 A | | 4/2000 | Loeb et al. |
| 6,058,332 A | | 5/2000 | Dahl |
| 6,181,969 B1 | | 1/2001 | Gord |
| 6,181,973 B1 | * | 1/2001 | Ceron et al. ................. 607/126 |
| 6,188,932 B1 | | 2/2001 | Lindegren |
| 6,201,994 B1 | * | 3/2001 | Warman et al. .............. 607/123 |
| 6,463,335 B1 | | 10/2002 | Munch et al. |
| 6,516,227 B1 | | 2/2003 | Meadows et al. |
| 6,584,363 B2 | * | 6/2003 | Heil et al. .................... 607/126 |
| 6,600,956 B2 | | 7/2003 | Maschino et al. |
| 6,609,029 B1 | | 8/2003 | Mann et al. |
| 6,609,032 B1 | | 8/2003 | Woods et al. |
| 6,643,546 B2 | * | 11/2003 | Mathis et al. ...................... 607/9 |
| 6,650,943 B1 | | 11/2003 | Whitehurst et al. |
| 6,735,474 B1 | | 5/2004 | Loeb et al. |
| 6,741,892 B1 | | 5/2004 | Meadows et al. |
| 6,788,975 B1 | | 9/2004 | Whitehurst et al. |
| 2003/0078623 A1 | * | 4/2003 | Weinberg et al. .................. 607/9 |
| 2004/0034401 A1 | * | 2/2004 | Dahlberg et al. ............ 607/125 |
| 2004/0059392 A1 | | 3/2004 | Parramon et al. |
| 2004/0230280 A1 | * | 11/2004 | Cates et al. .................... 607/126 |
| 2005/0065589 A1 | * | 3/2005 | Schneider et al. ............ 607/126 |
| 2005/0177220 A1 | * | 8/2005 | Iaizzo et al. .................. 607/126 |
| 2005/0182472 A1 | * | 8/2005 | Wahlstrom et al. ........... 607/126 |
| 2006/0161204 A1 | | 7/2006 | Colvin et al. |
| 2006/0184204 A1 | | 8/2006 | He |
| 2006/0212075 A1 | | 9/2006 | Marnfeldt |
| 2006/0241737 A1 | | 10/2006 | Tockman et al. |
| 2007/0129780 A1 | | 6/2007 | Whitehurst et al. |
| 2007/0142889 A1 | | 6/2007 | Whitehurst et al. |
| 2007/0150007 A1 | | 6/2007 | Anderson et al. |
| 2007/0150036 A1 | | 6/2007 | Anderson |
| 2007/0161294 A1 | | 7/2007 | Brase et al. |
| 2007/0219595 A1 | | 9/2007 | He |
| 2007/0239243 A1 | | 10/2007 | Moffitt et al. |

FOREIGN PATENT DOCUMENTS

| | | |
|---|---|---|
| WO | 98/43700 | 10/1998 |
| WO | 98/43701 | 10/1998 |

OTHER PUBLICATIONS

Rattay, F., "Analysis of Models for External Stimulation of Axons," IEEE Transactions on Biomedical Engineering, BME-33(10): 974-977, 1986.

* cited by examiner

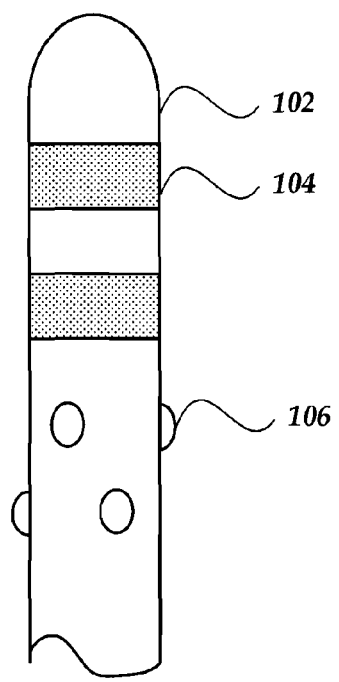
Fig. 1
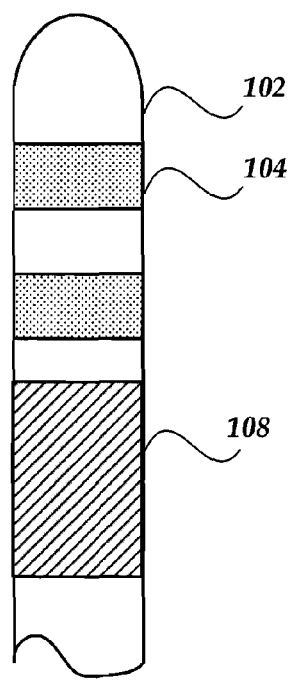
Fig. 2
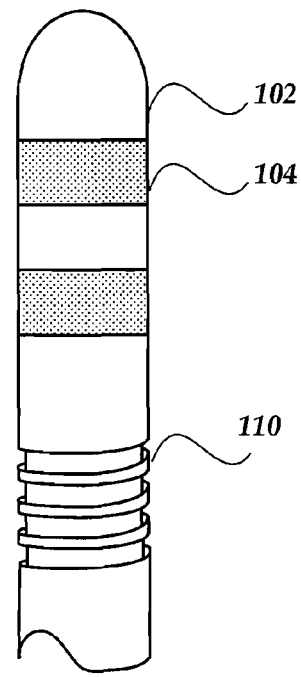
Fig. 3
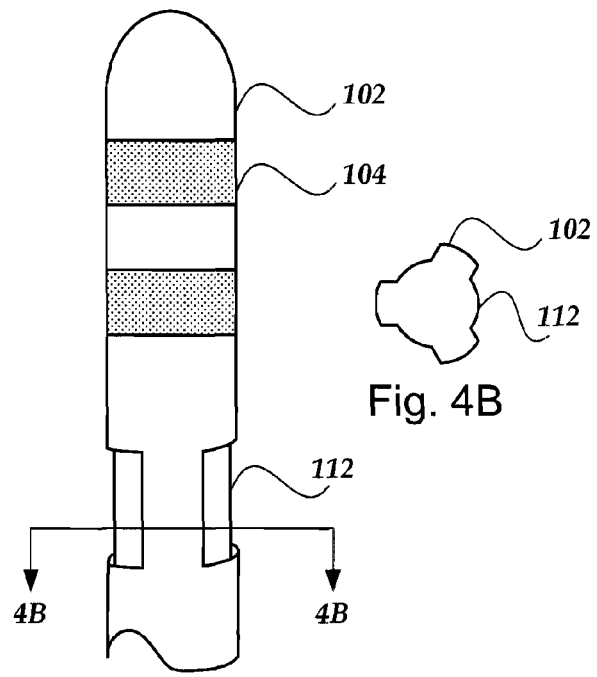
Fig. 4A
Fig. 4B

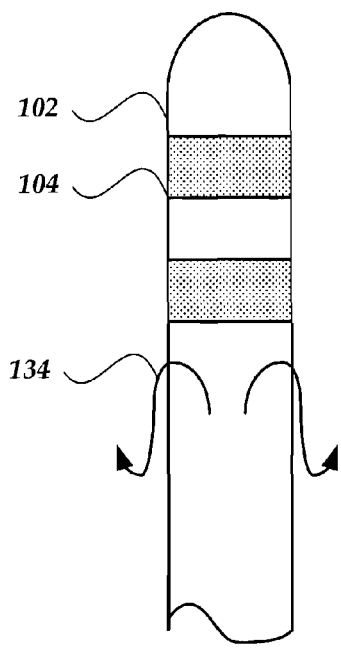
Fig. 13
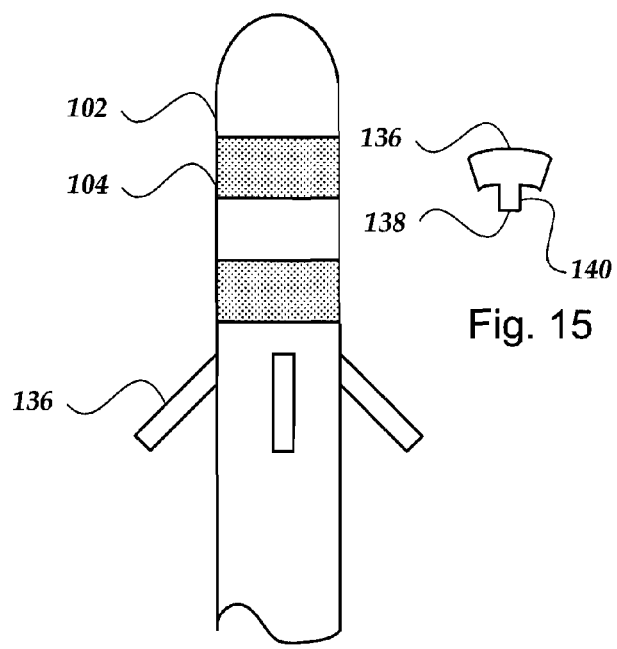
Fig. 15
Fig. 14
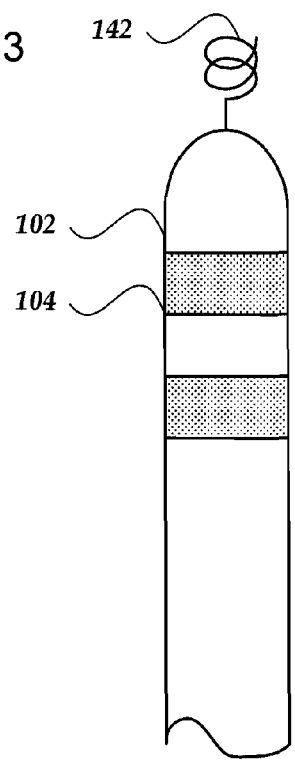
Fig. 16
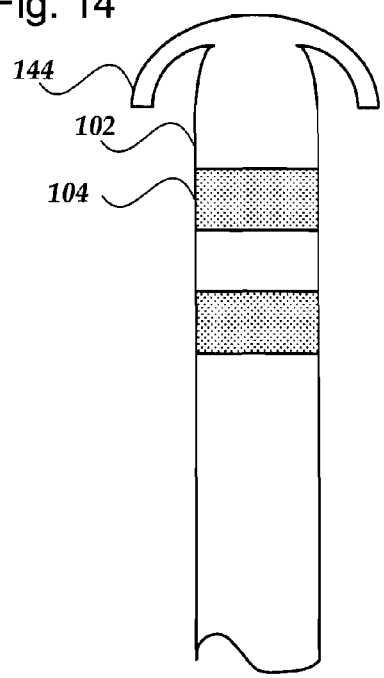
Fig. 17

US 8,244,377 B1

FIXATION ARRANGEMENTS FOR IMPLANTABLE LEADS AND METHODS OF MAKING AND USING

CROSS-REFERENCE TO RELATED APPLICATIONS

The present patent application claims benefit of U.S. Provisional Patent Application Ser. No. 60/827,199, which is incorporated herein by reference.

FIELD

The invention is directed to implantable leads that include fixation arrangements, and methods of making and using the devices. In addition, the invention is directed to implantable leads having one or more fixation arrangements and methods of making and using the leads.

BACKGROUND

Implantable electrical stimulation devices have proven therapeutic in a variety of diseases and disorders. For example, pacemakers and implantable cardiac defibrillators have proven effective in the treatment of cardiac conditions. Spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Implantable drug delivery systems allow highly concentrated drugs to be delivered to specific sites. This site specific delivery can result in reduced side effects, improved quality of life, and, in some cases, may extend life. Such drug delivery systems include both programmable pumps and constant flow pumps. Examples of such systems include intrathecal drug delivery for the treatment of chronic intractable pain; delivery of baclofen for the treatment of spasticity; site specific delivery of drugs for the treatment of cancer, and site specific insulin delivery for the management of diabetes.

One disadvantage of these devices is that the electrode lead or drug catheter may migrate within the body. Migration may result in failure of the therapy or cause unwanted side effects. For example, some nerves are located next to or within muscles that may cause movement of the lead or catheter. Actuation of limbs may exert unequal pressures which can also cause migration. Some nerves are near or within firm, but lubricious, tissue. For example, the vagus nerve runs through the carotid sheath in the neck and is surrounded by a number of muscles which can cause migration of an implanted lead or catheter. The firm, lubricious carotid sheath may offer little adhesion to a lead or catheter and actuation of the surrounding neck muscles may cause significant migration especially during the period immediately following implantation.

BRIEF SUMMARY

One embodiment is an implantable member having a body with a distal end portion and a fixation portion of the body disposed near the distal end portion. The fixation portion includes at least one surface feature of the body that facilitates fixation of the implantable member within tissue when implanted.

Another embodiment is an implantable member having a body with a distal end portion and a fixation device attached to a tip of the distal end portion of the body.

Yet another embodiment is a stimulation system that includes either of the implantable members described above with at least one electrode disposed on the implantable member and a processor for directing electrical signals to the electrode(s).

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 1 is a schematic side view of one embodiment of an implantable lead, according to the invention;

FIG. 2 is a schematic side view of a second embodiment of an implantable lead, according to the invention;

FIG. 3 is a schematic side view of a third embodiment of an implantable lead, according to the invention;

FIG. 4A is a schematic side view of a fourth embodiment of an implantable lead, according to the invention;

FIG. 4B is a cross-sectional view of the implantable lead of FIG. 4A;

FIG. 13 is a schematic side view of a thirteenth embodiment of an implantable lead, according to the invention;

FIG. 14 is a schematic side view of a fourteenth embodiment of an implantable lead, according to the invention;

FIG. 15 is a cross-sectional view of one embodiment of a tine for use with the implantable lead of FIG. 14.

FIG. 16 is a schematic side view of a fifteenth embodiment of an implantable lead, according to the invention;

FIG. 17 is a schematic side view of a sixteenth embodiment of an implantable lead, according to the invention;

DETAILED DESCRIPTION

Figure 5:
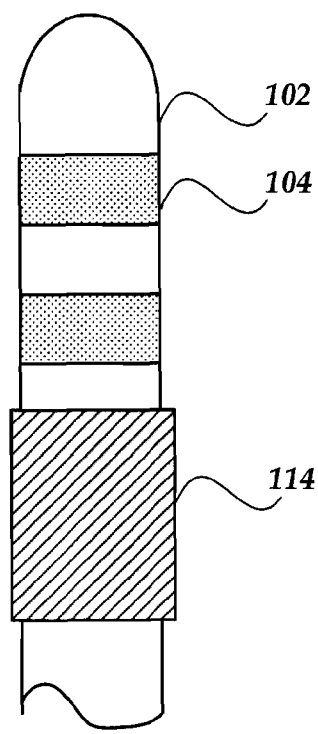
FIG. 5 is a schematic side view of a fifth embodiment of an implantable lead, according to the invention.

The invention is directed to implantable leads that include fixation arrangements, and methods of making and using the devices. In addition, the invention is directed to implantable leads having one or more fixation arrangements and methods of making and using the leads.

Suitable implantable devices include, but are not limited to, electrode leads, microstimulators, catheters, and sensors. For example, the implantable device can be an electrode lead with one or more electrodes disposed on a distal end of the lead and one or more terminals disposed on a proximal end of the lead. Electrodes leads include, for example, percutaneous leads and paddle leads. Examples of stimulation systems with electrode leads are found in, for example, U.S. Pat. Nos. 6,181, 969; 6,516,227; 6,609,029; 6,609,032; and 6,741,892; and U.S. patent application Ser. Nos. 11/238,240; 11/319,291; 11/327,880; 11/375,638; 11/393,991; and 11/396,309, all of which are incorporated by reference.

A fixation arrangement can also be used to fix a microstimulator in place. Examples of suitable microstimulators are described in U.S. Pat. Nos. 5,193,539; 5,193,540; 5,312, 439; and 6,051,017; U.S. Patent Application Publication No. 2004/059392; U.S. patent application Ser. Nos. 11/040,209; 11/056,762; 11/084,368; and 11/238,240 and PCT Patent Applications Publication Nos. 98/37926; 98/43700; and 98/43701, all of which are incorporated herein by reference. The BION™ microstimulator, available from Advanced Bionics Corporation, Sylmar, Calif., is an example of a microstimulator.

A fixation arrangement can also be used to fix a catheter in place. For example, the catheter can be a part of an implantable drug delivery system. The catheter is typically implanted in the proximity of the tissue to be treated. A catheter typically includes a catheter body surrounding one or more lumens and defining one or more openings near a distal end of the catheter body to allow flow of material into, or out of, a patient.

Implantable sensors can also be fixed using a fixation arrangement. Examples of sensors include, but are not limited to, electrical activity sensors (e.g., electroencephalograph, electrocardiograph, electromygraph, and electronystagmograph sensors); chemical sensors (e.g., glucose and drug sensors); and mechanical activity sensors (e.g., pressure, strain, stress, position, velocity, and acceleration sensors.)

These types of implantable devices can also be combined. For example, an electrode lead may also include a catheter lumen to provide drugs or other medications to the tissue to be stimulated or to other proximate tissue. As another example, an electrode lead can include one or more of the sensors described above. Yet another example is a catheter that includes one or more of the above-described sensors.

For purposes of illustration, an electrode lead will be used in the description below. It will be readily apparent that the electrode lead can be replaced with a microstimulator, catheter, or sensor lead in the embodiments below and that the described fixation arrangements can be adapted to such devices.

A variety of fixation arrangements can be used including arrangements that are disposed on the surface of the lead and, preferably, near the electrodes at the distal end of the lead, as well as arrangements that are disposed at the distal tip of the lead. Some arrangements provide surface features that assist fixation of the lead upon implantation and resist movement of the lead within the tissue. Other arrangements affect the surrounding tissue to increase fixation or promote tissue ingrowth into, or onto, portions of the lead. Some arrangements provide anchors in the tissue for the lead. It will also be recognized that the fixation methods described herein can be used together in any combination.

Each of the embodiments illustrated in FIGS. 1-15 include features that can be provided near the distal end of the lead including nearer to the distal end than the electrodes, nearer the proximal end than the electrodes, between electrodes, or any combination thereof.

FIG. 1 illustrates one embodiment of a lead 102 that includes one or more electrodes 104 disposed on the lead. It will be recognized that this embodiment (as well as all other embodiments of a lead body illustrated in the Figures) can be modified for use as a microstimulator, a catheter with one or more openings at or near the distal end, or a sensor with one or more sensor electrodes instead of lead electrodes.

The lead body can be made of any suitable material including, metal, plastic, and the like, or combinations thereof. Generally, the lead body is made using a biocompatible material.

The electrode(s) 104 are generally formed using a conductive material such as metal, graphite, conductive polymer and the like, or any combination thereof. The electrode(s) can take the form of, for example, ring electrode(s), as illustrated in FIG. 1, or one electrode may form the tip of the lead, or the electrode(s) can be partial rings, or any combination thereof. Other electrode configurations can be used as well. If there is more than one electrode, the electrodes can be spaced in any regular or irregular arrangement.

The electrode(s) at the distal end of the lead 102 are typically coupled to corresponding terminal(s) (not shown) at a proximal end of the lead using conductors (not shown) that traverse the length of the lead within the lead body. If there is more than one electrode, individual electrodes can be coupled to individual conductors, or one or more of the electrodes can be coupled to the same conductor, or any combination thereof. The terminals of the lead can be coupled to an implantable pulse generator or any other suitable device for providing electrical signals to the lead to provide the desired tissue stimulation.

The embodiment of FIG. 1 includes one or more protuberances 106 that extend from a surface of the lead 102, preferably, near the electrode(s) 104 and, preferably, near a distal end of the lead. If there is more than one protuberance, the protuberances can be arranged in any manner including regularly or irregularly and can be arranged, for example, primarily on one side of the lead or relatively balanced around the lead. The protuberances can be positioned, for example, in one or more columns or rows (e.g., rings) on the lead. In one embodiment, the protuberances are spaced at regular intervals in one or more ring-like arrangements around the lead, as illustrated, for example, in FIG. 1.

The height of the protuberances 106 away from the surface of the lead 102, as well as the width and length of the protuberances, can be selected to provide a desired amount of fixation. The protuberances can have a uniform size and shape or can vary in size or shape or both. The protuberances can have any regular or irregular shape such as, for example, hemispherical, spherical, cubic, parallelepiped, pyramidal, or other shapes. The protuberances 106 can be formed of the same material as the lead body or from a different material. The protuberances can be formed integrally with the lead body or attached using any suitable attachment method.

The embodiment of FIG. 2 includes a region 108 of the lead body that is roughened. The region 108 can, for example, increase the friction of the lead body with surrounding tissue or promote in-growth of tissue to fix the lead body within the patient. The region 108 may be knurled or include indentations, scratches, or other irregular or regular marks. As one example, knurling marks, such as lines (straight or diagonal), diamonds, and the like, can be formed on the surface of the lead body. The roughened surface can be made by any method including, but not limited to, molding the lead body with the roughened surface, or scoring, scratching, sanding, sand blasting, cutting, etching, or knurling the surface.

In an alternative embodiment, the region 108 can be coated instead, or in addition to roughening, with a material that promotes tissue adhesion, such as expanded polytetrafluoroethylene (ePTFE), fibrin glues (e.g., Tissel™ or Hemaseel™), gelatin adhesives (e.g., gelatin dialdehyde or a gelatin-resorcinol mixture crosslinked with formaldehyde), or other medical adhesives, or a material that promotes scar tissue formation, such as nylon, metals, silicone, or polyurethane. Such materials can assist in attachment of the surrounding tissue to the lead body. The region 108 of the lead body can be precoated, optionally with a release liner (not shown) over the coating that can be removed prior to implantation, or the region of the lead body can be coated as part of the implantation process. Instead of a coating, a portion, or all, of the lead body can be made of a material that is naturally tacky at body temperature, such as low durometer silicone (for example, about 25 durometer or less) to facilitate fixation in the tissue.

In another alternative embodiment, the region 108 can include a conductive or resistive patch with associated conductors that run the length of the lead. Electrical signals can be applied to heat the patch and burn the surrounding tissue. The coagulated or charred tissue can stick to the lead or promote scar tissue formation that can adhere to the lead. Burning of the tissue can be performed using, for example, rf lesioning or resistive heating techniques.

FIG. 3 illustrates an embodiment containing a threaded portion 110 of the lead body. The threaded portion 110 can act as a screw or helical arrangement to provide edges that can hold the lead 102 in place within the tissue. In addition, or alternatively, tissue in-growth between the threads can facilitate fixation. The threaded portion can be formed in any manner including, but not limited to, molding the lead body with the threaded portion or cutting or otherwise removing material from the lead body to form the threaded portion.

FIGS. 4A and 4B illustrate an embodiment of a lead 102 with one or more indentations 112 (e.g., cutouts) formed in the lead surface to allow tissue to fill in the space during and after implantation or to allow tissue in-growth into the space over time. Any shape, length, width, and depth can be selected for the indentation(s). Factors in such a selection can include, for example, amount of tissue that can be incorporated in the indentations to provide fixation, weakening of the lead body as a result of the indentation(s), depth of the ridge of the indentation orthogonal to the long axis of the lead, wall thickness of the indentation, and the like. The indentation(s) can be formed in any manner including, but not limited to, molding the lead body with the indentation(s) or cutting or otherwise removing material from the lead body to form the indentations.

When more than one indentation 112 is provided, the indentations can be spaced longitudinally along the length of the lead body or around the lead body or in any combination thereof. The spacing can be regular or irregular. In the illustrated example in FIG. 4B, three indentations are provided and these indentations are spaced in a regular pattern around the lead body.

FIG. 5 illustrates an embodiment of a lead 102 with a sleeve 114 of material that assists in fixation of the lead to tissue. The sleeve can be attached to the lead body by adhesive, friction fit, or any other attachment mechanism. In one embodiment, the sleeve 114 is made of a material that permits or may even encourages in-growth of tissue into the sleeve. One example of such a material is expanded polytetrafluoroethylene (ePTFE). In another embodiment, the sleeve forms a netting that allows (or may even be formed of, or coated with, a material that encourages) in-growth of tissue around, and through, the netting. In yet another embodiment, the sleeve 114 can be formed of material that expands upon exposure to body fluids. Typically, the sleeve is made of a biocompatible material.

Figure 6:
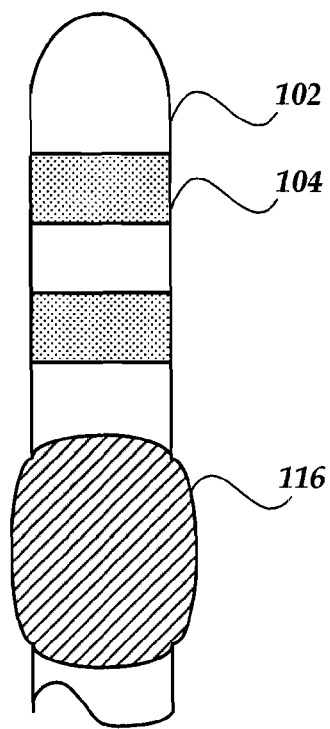
FIG. 6 is a schematic side view of a sixth embodiment of an implantable lead, according to the invention.

FIG. 6 illustrates an embodiment of a lead 102 with one or more expandable features 116, such as bubbles, bumps, tines, and the like, disposed on the body of the lead. The expandable feature(s) can be inflated prior to or, preferably, after implantation. The inflation can occur using any liquid or fluid inflatant including, but not limited to, air, oxygen, water, saline, and the like.

As an alternative, the expandable feature(s) can be expanded using a piezoelectric device that is typically coupled to conductors that run the length of the lead body to terminals at the proximal end of the lead. Electrical signals can be provided to the piezoelectric devices via the terminals and conductors to cause the expansion of the expandable features 116. Optionally, electrical signals can also be provided during, for example, explantation to contract the expandable features 116.

In another embodiment, the expandable feature(s) 116 can be formed of a material that expands, or otherwise changes shape, upon heating to body temperature. Such materials include nitinol and thermoplastic materials. In yet another embodiment, the expandable feature(s) can be made of material that absorbs fluid from the body to expand.

The expandable feature(s) can take any regular or irregular shape including, but not limited to, spherical, ring-like, helical, or tine-like shapes. When more than one expandable feature is provided, the expandable features can be disposed in any regular or irregular arrangement on the lead body. For example, the expandable features may be disposed in one or more ring-like arrangements around the circumference of the lead body.

Figure 7:
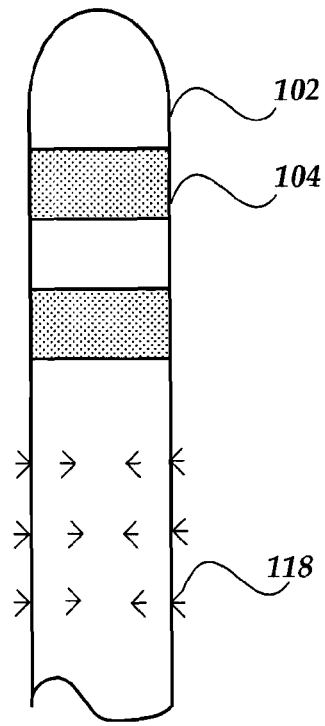
FIG. 7 is a schematic side view of a seventh embodiment of an implantable lead, according to the invention.

FIG. 7 illustrates an embodiment of a lead 102 with one or more bristles 118 disposed on the surface of the lead. These bristles may be regularly or irregularly spaced upon a portion of the surface of the lead. Optionally, multiple bristles may be clustered together, as illustrated in FIG. 7. Any type of bristle can be used including, but not limited to, those that have a fractal-like fiber shape. The length, stiffness, and distribution of the bristle(s) can be selected to provide a desired range of fixation.

Figure 8:
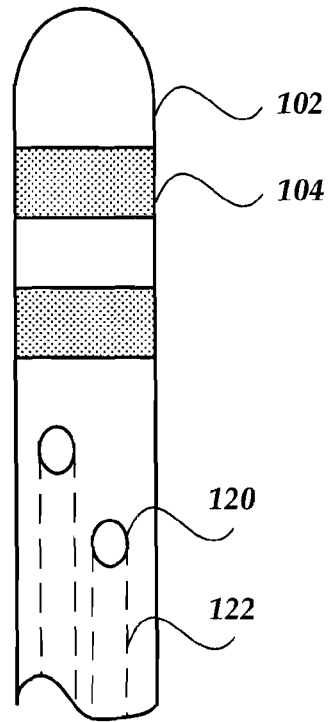
FIG. 8 is a schematic side view of an eighth embodiment of an implantable lead, according to the invention.

FIG. 8 illustrates an embodiment of a lead 102 that includes one or more lumens 122 traveling the length of the lead body and corresponding openings 120 in the lead body. A particular lumen can be associated with one or more openings. The lumens and openings can be used to inject a material through the lead during or after implantation. The injected material can be, for example, an adhesive material or a material that encourages scar tissue formation to promote fixation of the lead to the surrounding tissue. In a catheter embodiment, such material could instead be injected through the primary catheter lumen(s). When more than one opening 120 is used, the openings can be spaced in any regular or irregular pattern. In one embodiment, openings 120 are spaced in a regular pattern around the circumference of the lead 102.

In an alternative embodiment, the lumens 112 and openings 120 can be used to create a vacuum that draws surrounding tissue into or next to the openings 120. Optionally, corresponding lumen openings (not shown) at a proximal end of the lead, where a vacuum generating device can be attached to create the vacuum, can be sealed after generating the vacuum and drawing the tissue into contact with the openings 120. Sealing the openings at the proximal end can facilitate maintaining the vacuum within the lumen(s) 112.

Figure 9:
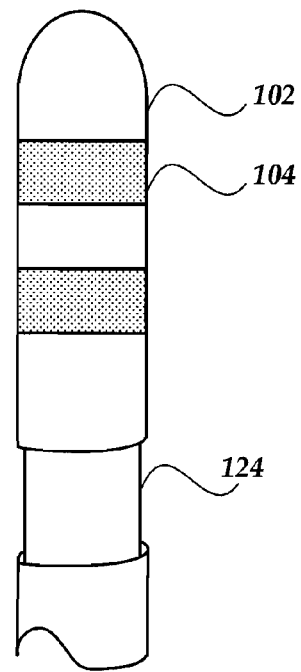
FIG. 9 is a schematic side view of a ninth embodiment of an implantable lead, according to the invention.
Figure 10:
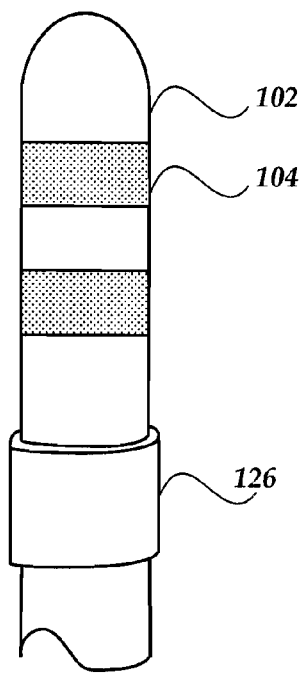
FIG. 10 is a schematic side view of a tenth embodiment of an implantable lead, according to the invention.

FIGS. 9 and 10 illustrate embodiments of a lead 102 that include one or more stepped regions 124, 126 of the lead body. In the embodiment of FIG. 9, the stepped region 124 is narrower than adjacent portions of the lead body. In the embodiment of FIG. 10, the stepped region 126 is wider than adjacent portions of the lead body. In other embodiments, multiple stepped regions can be used and may include regions wider than the lead body, regions narrower than the lead body, or combinations thereof. The stepped regions can increase friction with surrounding tissue and/or promote tissue in-growth around or within the stepped region. The stepped regions, and in particular the narrower stepped region 124, can also have one or more surface features such as, for example, bumps, spikes, bristles, barbs, or the like to provide additional fixation.

In an alternative embodiment, one or more of the electrodes can be stepped. For example, one or more of the electrodes can be wider or narrower in diameter than the adjacent lead body. This can again increase friction with surrounding tissue and/or promote tissue in-growth around or within the stepped electrode.

Figure 11:
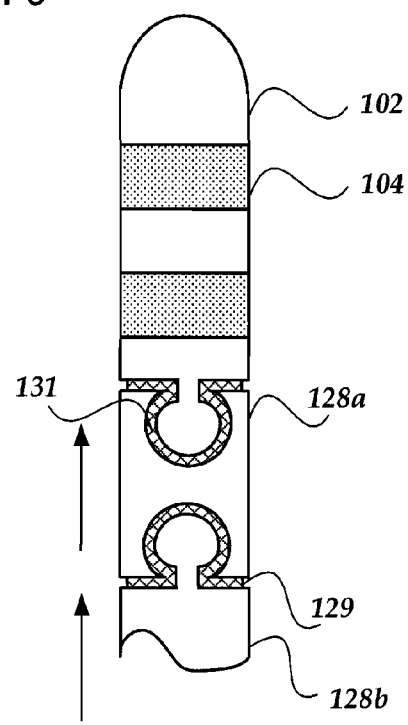
FIG. 11 is a schematic side view of an eleventh embodiment of an implantable lead, according to the invention.

FIG. 11 illustrates one embodiment of a lead 102 that includes one or more slidably engaged outer members 128a, 128b. These outer members are slidable over an interior lead body 129 (crosshatched in FIG. 11). When implanted, the outer members 128a, 128b are spaced apart to expose portions 131 of the interior lead body, as illustrated in FIG. 11. Tissue in-growth can occur in the exposed portions 131 to fix the lead in the tissue. When the lead is to be explanted, the outer members 128a, 128b can be slid along the lead body, if desired, (see arrows in FIG. 11) and over the exposed portions 131 of the interior lead body 129 to cut the in-grown tissue.

The outer members 128a, 128b can be formed in any shape including, but not limited to, a keyed shape such as the dove-tailed shape illustrated in FIG. 11, or a cylindrical shape. The dove-tailed shape provides additional space for in-growth of tissue which can be cut relatively easily by sliding the outer members 128a, 128b along the interior lead body 129. One embodiment includes two or more outer members 128 that are sequentially spaced along a portion of the lead body.

Figure 12:
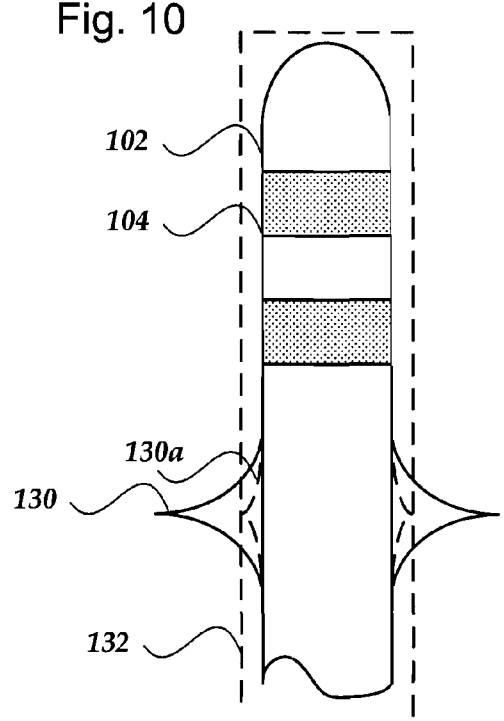
FIG. 12 is a schematic side view of a twelfth embodiment of an implantable lead, according to the invention.

FIG. 12 illustrates one embodiment of a lead 102 with one or more expandable fixation members 130. In at least some embodiments, the lead 102 is implanted into the tissue using an introducer 132. The lead 102 is inserted into the introducer which surrounds the lead 102 and includes a tip that can be pushed through the tissue to the implantation site. When the lead 102 is at the implantation sight, the introducer 132 is removed leaving the lead 102. During implantation, the fixation members 130 are held near the lead body as illustrated by the dotted lines 130a in FIG. 12. When the introducer 132 is removed, the fixation members 130 expand into the nearby tissue. In at least one embodiment, the fixation members 130 have a spring-like quality that results in the expansion of the members when the introducer 132 is removed. For example, the fixation members can be made of thin strips of resilient metal or plastic or a compressible bladder. When more than one fixation member is provided, the fixation members can be distributed in a regular or irregular pattern around the lead body.

FIG. 13 illustrates one embodiment of a lead 102 with one or more barbs 134 that extend form the surface of the lead. The barbs 134 can be hooked into surrounding tissue to fix the lead in place. In some embodiments, the end of the barb is made using a rigid material, such as stainless steel or another metal, to anchor in the tissue, but the remainder of the barb can be made of a flexible material, such as silastic, to facilitate implantation through an introducer.

FIG. 14 illustrates one embodiment of a lead 102 with one or more tines 136 that extend from the surface of the lead. The tines can be formed integral with the lead body or the tines can be attached to the lead body using any attachment method. The tines may be blunt or pointed. If more than one tine is provided, the tines can be distributed in any regular or irregular pattern around the lead body including, but not limited to, one or more ring-like arrangements around the lead body.

Optionally, the tines 136 can be made of a material, such as nitinol or a thermoplastic material, that changes shape during heating to body temperature. This allows the tines to be deployed after implantation. For example, in one embodiment, when cold and prior to implantation, the tines can rest near the lead body. When heated by the body after implantation, the tines can be deployed to extend away from the body.

In another embodiment, the tines are coupled to a piezoelectric device that can be controlled to deploy the tines after implantation.

In one embodiment, the tines 136 are shaped so that they can break away during explantation. FIG. 15 illustrates a cross-section of one embodiment of a break-way tine 136. The cross-section is taken at the end of the tine where it attaches to the lead body. In this embodiment, the tine 136 has a narrower portion 140 with a surface 138 that attaches to the lead body. This narrower portion can break-away during explantation to leave the tine within the patient's body when the lead is removed. Generally, the tine should be sturdy enough within the body for normal movement over a desired implantation period.

FIG. 16 illustrates one embodiment of a lead 102 with a pin 142 provided at a tip of the lead. The pin 142 can have any shape. In one embodiment, the pin has a helical shape and, optionally, the lead can be rotated during or after implantation to screw the helical pin into the tissue. Alternatively, the pin may be coupled to an internal shaft (not shown) that can be rotated to screw the pin into the tissue. In another embodiment, the pin can be, for example, straight or helically shaped and can include one or more barbs at the end to assist in fixation.

FIG. 17 illustrates one embodiment of a lead 102 with a shaped tip 144 that permits tissue in-growth between portions of the tip or between the tip and the lead body. Preferably the shaped tip is formed of material that is sufficiently flexible to be pushed through the insertion needle and yet still rigid enough to assist in fixation of the lead after tissue in-growth. The shape preferably includes one or more portions where tissue can grow and be surrounded on at least three sides by the lead body (including the shaped tip 144).

Figure 18:
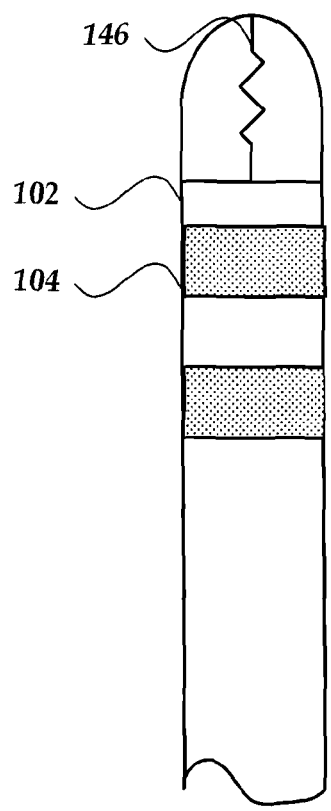
FIG. 18 is a schematic side view of a seventeenth embodiment of an implantable lead, according to the invention.
Figure 19A:
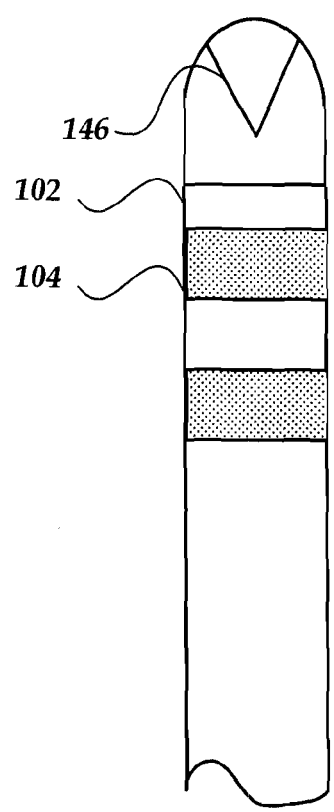
FIG. 19A is a schematic side view of a eighteenth embodiment of an implantable lead, according to the invention.
Figure 19B:
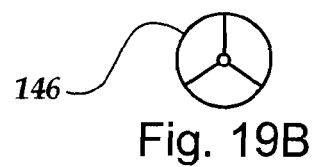
FIG. 19B is a schematic end view the implantable lead of FIG. 19A, according to the invention.

In other embodiments illustrated in FIGS. 18, 19A, and 19B, the lead 102 includes jaws 146 at the tip of the lead. The jaws can be engaged with the tissue manually by the physician during the insertion procedure or can be configured so that they are open within the introducer but close when the introducer is withdrawn or can be configured to close if the lead is retracted slightly.

Figure 20:
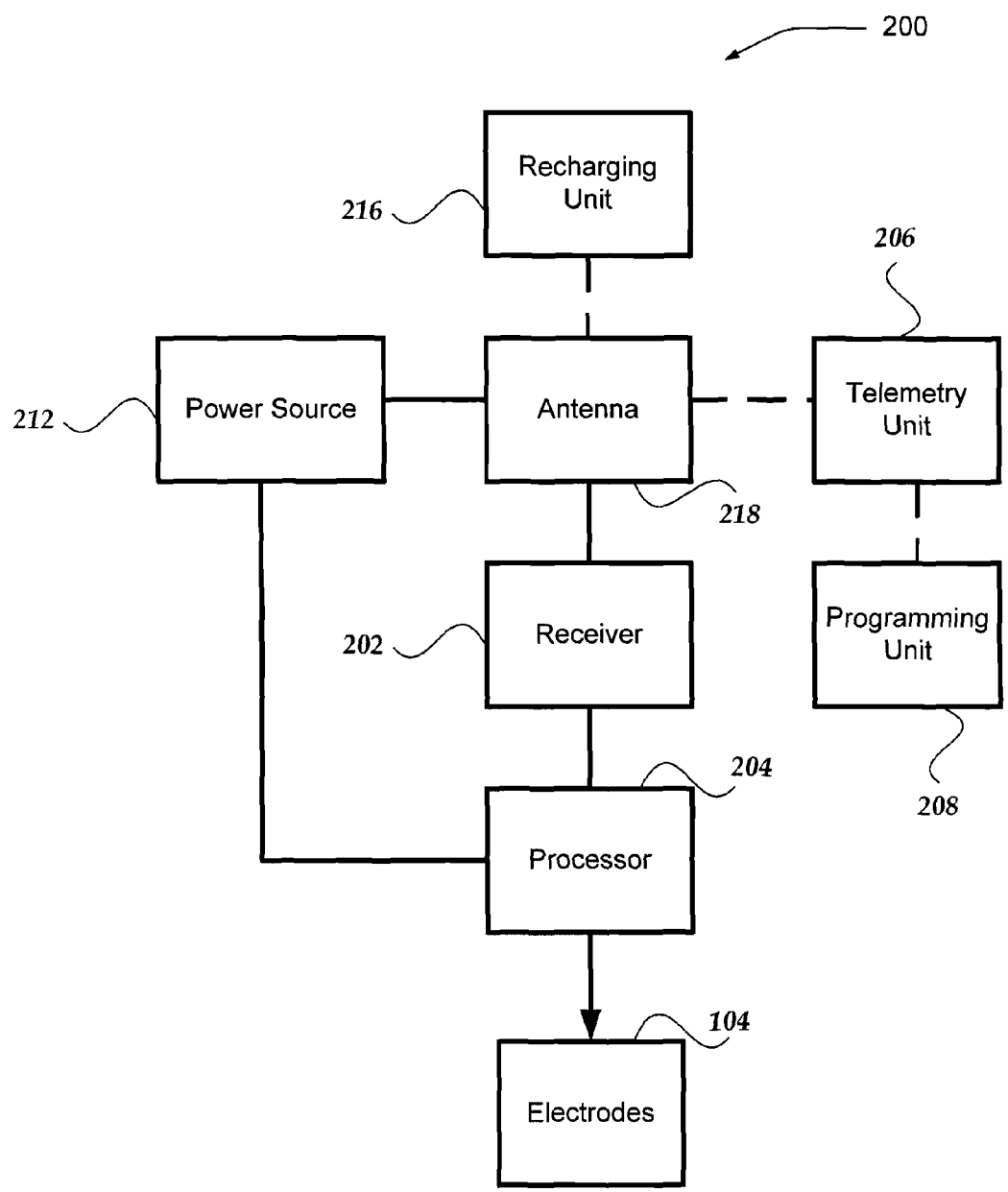
FIG. 20 is schematic block diagram of one embodiment of a stimulation system, according to the invention.

FIG. 20 is a schematic overview of one embodiment of components of a stimulation system 200. It will be understood that the stimulation system can include more, fewer, or different components and can have a variety of different configurations including those configurations disclosed in the stimulator references cited herein.

Some of the components (for example, power source 212, antenna 218, receiver 202, and processor 204) of the stimulation system can be positioned on one or more circuit boards or similar carriers within a housing of an implantable pulse generator, if desired. It will also be understood that similar components can be used in a microstimulator with the microstimulator including, for example, power source 212, antenna 218, receiver 202, processor 204, and electrodes 104 within, on, or as part of, a microstimulator housing. A catheter can be coupled, for example, to an implantable or external drug pump that can include, for example, one or more of power source 212, antenna 218, receiver 202, and processor 204. Similarly, a sensor lead can be coupled to an implantable or external sensor controller which can include, for example, one or more of power source 212, antenna 218, receiver 202, and processor 204.

Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 218 or a secondary antenna. The external power source can be in a device that is mounted on the skin of the user or in a unit that is provided near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 104 on the lead body to stimulate nerve fibers, muscle fibers, or other body tissues near the stimulation system. A processor 204 is generally included to control the timing and electrical characteristics of the stimulation system. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue. In the catheter embodiment, the processor can be used to, for example, manage delivery of a drug or other mediation. In the sensor embodiment, the processor can be used to, for example, monitor the sensors or activate/deactivate sensors. This process may be performed using an external programming unit, as described below, that is in communication with the processor 204.

Any processor can be used and can be as simple as an electronic device that, for example, produces pulses at a regular interval or the processor can be capable of receiving and interpreting instructions from an external programming unit 208 that, for example, allow modification of pulse characteristics. In the illustrated embodiment, the processor 204 is coupled to a receiver 202 which, in turn, is coupled to the optional antenna 218. This allows the processor to receive instructions from an external source to, for example, direct the pulse characteristics and the selection of electrodes, if desired.

In one embodiment, the antenna 218 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulation system. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 218 and receiver 202 can be used to modify or otherwise direct the operation of the stimulation system (or microstimulator or catheter or sensor). For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antennae 218 or receiver 202 and the processor 204 operates as programmed.

Optionally, the stimulation system may include a transmitter (not shown) coupled to the processor and antenna for transmitting signals back to the telemetry unit 206 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable member, comprising:
   a body comprising a distal end portion and a distal tip disposed at an end of the distal end portion;
   a plurality of electrodes disposed along the distal end portion and proximal to the distal tip of the body; and
   a fixation portion of the body disposed near the distal end portion and proximal to the plurality of electrodes, wherein the fixation portion comprises at least one surface feature of the body that facilitates fixation of the implantable member within tissue when implanted, wherein the at least one surface feature comprises a plurality of bumps disposed on the body, each of the bumps having a hemispherical, spherical, cubic, or pyramidal shape.

2. The implantable member of claim 1, wherein the plurality of electrodes comprises at least one ring electrode.

3. The implantable member of claim 1, wherein the plurality of bumps are disposed on the body in a plurality of rows, each row extending around the circumference of the body at a different position along a length of the body.

4. The implantable member of claim 1, wherein the at least one surface feature comprises a roughened surface comprising a plurality of scratches or lines formed in the surface.

5. The implantable member of claim 1, wherein the at least one surface feature comprises a sleeve disposed over a portion of the body.

6. The implantable member of claim 1, wherein the at least one surface feature comprises at least one expandable feature that is configured and arranged for inflation upon exposure to body fluids.

7. The implantable member of claim 1, wherein the at least one surface features comprises a plurality of fiber-like bristles extending from the lead body.

8. The implantable member of claim 1, wherein the at least one surface feature comprises a surface configured and arranged to burn surrounding tissue upon application of an electrical signal.

9. The implantable member of claim 1, wherein the at least one surface feature comprises a chemical coating configured and arranged to adhere to tissue or cause scar tissue formation.

10. The implantable member of claim 1, wherein the at least one surface feature comprises at least one opening and wherein the implantable member comprises at least one lumen extending through the lead body to the at least one opening and further comprising an injection material configured and arranged for injection through the at least one lumen to adhere to tissue or cause scar tissue formation.

11. The implantable member of claim 1, wherein the at least one surface feature comprises a stepped region formed in the lead body, wherein the stepped region is wider than adjacent portions of the lead body.

12. The implantable member of claim 1, wherein the lead body comprises an interior lead body and the at least one surface feature comprises at least one slidably engaged outer member slidable over the interior lead body and configured and arranged to expose the interior lead body to allow tissue in-growth.

13. A stimulation system comprising the implantable member of claim 1 and further comprising a processor for directing electrical signals to the at least one electrode.

* * * * *